US007712288B2

(12) United States Patent
Ramasubramanian et al.

(10) Patent No.: US 7,712,288 B2
(45) Date of Patent: May 11, 2010

(54) UNIFIED INGESTION PACKAGE AND PROCESS FOR PATIENT COMPLIANCE WITH PRESCRIBED MEDICATION REGIMEN

(76) Inventors: Narayanan Ramasubramanian, 48873 Semillon Dr., Fremont, CA (US) 94539; Anand Subra, 2545 Weston La., Plymouth, MN (US) 55447

( * ) Notice: Subject to any disclaimer, the term of this patent is extended or adjusted under 35 U.S.C. 154(b) by 950 days.

(21) Appl. No.: 11/140,012

(22) Filed: May 27, 2005

(65) Prior Publication Data

US 2005/0267356 A1    Dec. 1, 2005

Related U.S. Application Data

(60) Provisional application No. 60/575,488, filed on May 28, 2004, provisional application No. 60/577,319, filed on Jun. 3, 2004.

(51) Int. Cl.
    *B65B 57/00* (2006.01)
(52) U.S. Cl. .............................. 53/507; 53/412; 53/467; 53/474; 53/475; 53/77; 386/10
(58) Field of Classification Search ................. 53/412, 53/467, 475, 484, 77, 507; 386/10
    See application file for complete search history.

(56) References Cited

U.S. PATENT DOCUMENTS

| 4,402,402 | A | | 9/1983 | Pike ............................ 206/219 |
| 5,839,257 | A | | 11/1998 | Soderstrom et al. ........... 53/411 |
| 5,852,590 | A | * | 12/1998 | de la Huerga ................ 368/10 |
| 6,004,927 | A | * | 12/1999 | Benet et al. ..................... 514/9 |
| 6,092,660 | A | | 7/2000 | Rune et al. ................... 206/534 |
| 6,256,967 | B1 | | 7/2001 | Hebron et al. ................ 53/501 |
| 6,270,804 | B1 | | 8/2001 | Getz et al. ................... 424/490 |
| 6,312,728 | B1 | | 11/2001 | Beiman et al. .............. 424/490 |
| 6,333,050 | B2 | | 12/2001 | Wong et al. ................. 424/473 |
| 6,347,705 | B1 | | 2/2002 | Futrell ......................... 206/534 |
| 6,370,841 | B1 | | 4/2002 | Chudy et al. ................... 53/411 |
| 6,537,578 | B1 | | 3/2003 | Bhagwat et al. ............. 424/488 |
| 6,589,551 | B1 | | 7/2003 | Jolliffe ........................ 424/451 |
| 6,605,300 | B1 | | 8/2003 | Burnside et al. ............ 424/452 |
| 6,625,952 | B1 | | 9/2003 | Chudy et al. ................. 53/168 |
| 6,663,846 | B1 | | 12/2003 | McCombs et al. ........... 424/9.2 |
| 6,742,671 | B2 | | 6/2004 | Hebron et al. ................ 221/9 |

(Continued)

OTHER PUBLICATIONS

Notification of Transmittal of the International Search Report and the Written Opinion of the International Searching Authority, or the Declaration for corresponding International application No. PCT/US05/18796.

*Primary Examiner*—Christopher Harmon
(74) *Attorney, Agent, or Firm*—Hickman Palermo Truong & Becker LLP (57) ABSTRACT

Techniques for reducing non-compliance of medication use are described. The techniques involve generating and storing an identifier for a specific dosage instance of a specific patient, and creating a package that includes a mechanism for conveying the identifier. Once the package is created, a set of one or more medications that are prescribed to be taken by the specific patient at the specific dosage instance are placed in the package. The set of medications within the package in a manner that prevents the identifier from being perceived from the mechanism until the package is opened. Once opened, the identifier is perceived and communicated back to an automated compliance system.

20 Claims, 5 Drawing Sheets

U.S. PATENT DOCUMENTS

| | | | |
|---|---|---|---|
| 6,761,895 B2 | 7/2004 | Sawada et al. | 424/400 |
| 6,839,304 B2 | 1/2005 | Niemiec et al. | 368/10 |
| 7,061,831 B2 * | 6/2006 | De La Huerga | 368/10 |
| 7,317,967 B2 * | 1/2008 | DiGianfilippo et al. | 700/265 |
| 2001/0017817 A1 * | 8/2001 | De La Huerga | 368/10 |
| 2002/0017996 A1 | 2/2002 | Niemiec | 340/573.1 |
| 2003/0063524 A1 | 4/2003 | Niemiec et al. | 368/10 |

* cited by examiner

Compliance Tracking and Management System

FIG. 6

UNIFIED INGESTION PACKAGE AND PROCESS FOR PATIENT COMPLIANCE WITH PRESCRIBED MEDICATION REGIMEN

RELATED APPLICATIONS

This application claims priority to the following provisional applications, the entire contents of which are incorporated herein by this reference:

U.S. Provisional Patent Application No. 60/575,488, filed by Narayanan Ramasubramanian on May 28, 2004, entitled "Patient-Specific Medication Preparation"; and U.S. Provisional Patent Application No. 60/577,319, filed by Narayanan Ramasubramanian on Jun. 3, 2004, entitled "Patient-Specific Medication Preparation".

FIELD OF THE INVENTION

The present invention relates to medication regimes and, more specifically, to techniques and systems to assist compliance with those regimes.

BACKGROUND

In many oral medication regimes, patients or experimental subjects are required to take multiple oral medications and/or doses at specified intervals during the day. There are several reasons why such patients do not comply with their regimens, but a large percentage (1) simply forget, (2) cannot get prescriptions filled or delivered, or (3) do not like the side effects. It is common for such patients to forget to take the medications at the proper time or even to take multiple doses because of difficulties in remembering what they have already taken. The risks of not complying with the prescribed regimens and suffering the symptoms of under-dosing or over-dosing are well documented. The costs of treating the resulting medical problems have been estimated at over $100 billion per year in the US alone.

A large factor in the lack of compliance is inconvenience. While bottles are ideal as a delivery system for tablets or capsules from the pharmacy to the patient, they are not conducive to patient compliance. The inconvenience for a given patient increases dramatically with: (1) the number of medications in separate containers that the patient has to take, (2) the number of daily repetitions of each medication, (3) the complexity of the rules governing the how and when to take the medications, especially if some have to be taken during normal sleeping times, or with food, or on an empty stomach, and (4) under-dosing or the side-effects that arise out of the slight overdosing because the medications can only be roughly titrated to the specific patient's metabolism (in order to balance efficacy and side-effects). This is because medications are available only in certain dosages in relatively large increments.

Products and services have been introduced to the market in an attempt to improve compliance. There are online services that offer free or fee-based automated reminders on a daily or other user-selected basis, via email or cell phone, to remind patients to take their medicines (such as services offered by Freeminder.com and Iping.com). Over time, some patients begin to ignore the reminders, while others dislike the 'automated' nature of the reminders and prefer a 'human touch'.

Some existing solutions also provide a multi-dose package containing all the medications to be taken by a particular patient at a particular time of day. These take the form of cups containing pills and capsules such as in the MD2 product from E-Pill.com, and rely on caregivers to fill the containers with the appropriate medications, leaving open the possibility of errors, especially for complex regimens. In some cases, reminders may be programmed into a device by the patient or caregiver. Some solutions automate the process of dispensing the appropriate pills and capsules, such as a system described in U.S. Pat. No. 5,839,257, and rely on a nurse or other licensed practitioner to administer the multi-dose to the patient and record the compliance event, typically in a hospital or managed facility setting. Due to cost and other factors, these may not be suited for patient self-administration. Yet other solutions use specially constructed blister packaging incorporating specialized electronics to detect compliance events. Some even provide remote dispensing of medications of different dosage strengths. These solutions are expensive since they rely on proprietary packaging and do not provide the convenience of a single package. There are also combinations of multiple drugs into a single pill or capsule, referred to as 'cocktail' therapy, but due to size limitations, these are usually for a single disease.

More recently, electronics-enabled blister packs have become available—these provide multiple medications and automated compliance recording, but are either expensive or have size limitations and thus may not be able to handle complex regimens. Other solutions such as a 'Smart Tray' with embedded RFID enabled medication containers, record which medication vials are removed from the tray and the time of removal; the data are transmitted to an online database as compliance events. In yet another solution, each medication vial is fitted with an RFID enabled detector that records the opening of the vial as a compliance event. The drawback in recording the opening of each container is that the patient still has to open each individual vial and manually assemble the requisite pills or capsules before taking them. In addition, the amount of data recorded is dependent on the number of containers rather that just the act of opening a single package. In many of the above cases, a special device or computer interface hardware and software must also be provided to patients, posing limits on scalability and speed of adoption.

In general, the above solutions address specific parts of the overall problem and have thus far failed to make a significant impact on patient compliance. The system described hereafter builds on some of these existing solutions, or parts thereof, to provide a more comprehensive solution.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Overview

Techniques and systems are described hereafter for reducing non-compliance by (1) reminding patients to take their medicines at the appropriate times, (2) simplifying the taking of medicines through personalized and convenient multi-dose packaging, (3) incorporating features in the packaging to enable the monitoring of patient compliance events, (4) monitoring and recording patient compliance events in a database, (5) analyzing the database to guide interventions to improve patient compliance, (6) analyzing the actual consumption of the medications to (a) automatically refill and deliver a labeled multi-day (15, 30 or 90 days) supply of medication packages to patients, and (b) more accurately forecast future drug production requirements, and (7) personalizing the dosage strengths to minimize side effects while maximizing the therapeutic effects.

System Overview

A comprehensive system is provided for reducing non-compliance. The system includes: (1) a patient-centric package of medications with a built-in compliance feature, and methods of using the said package, (2) a compliance tracking and management system comprised of: (a) a reminder service, (b) methods to capture patient compliance events, (c) a portal to receive compliance event data and to provide secured user access, (d) a secured database to hold the patient compliance records, (e) methods for handling non-compliance, and (f) a set of control programs and decision support programs that operate on the compliance records, and (4) specialized equipment produce the patient-centric packages. The system and its elements are described below.

Overview of Figures

Figure 1:
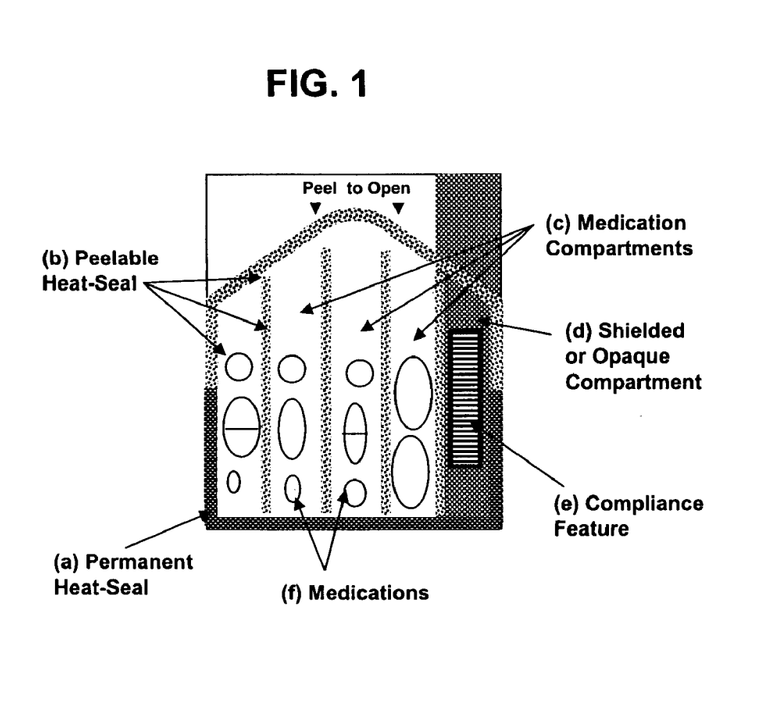
FIG. 1 illustrates a unified ingestion package, according to an embodiment of the invention.

FIG. 1 shows one embodiment of the 'unified ingestion package'. The package is constructed out of two rectangular sheets of flexible plastic film that are fastened together by means of a permanent heat-seal (a). The package also has peel-able heat-seal lines that seal in the contents but allow the two sheets to be separated along the said lines (b), and medication compartments (c) formed by multiple adjacent peel-able heat-seal lines. At least one of the compartments (d) is lined with opaque or shielding material in order to prevent the information embedded in the compliance feature (e) from being perceived without separating the sheets, i.e., opening the package. The compliance feature (e) may be in the form of a card with information printed on it, either as text or barcode that is glued to one of the sheets, or encoded on a magnetic strip or an RFID Tag.

Figure 2:
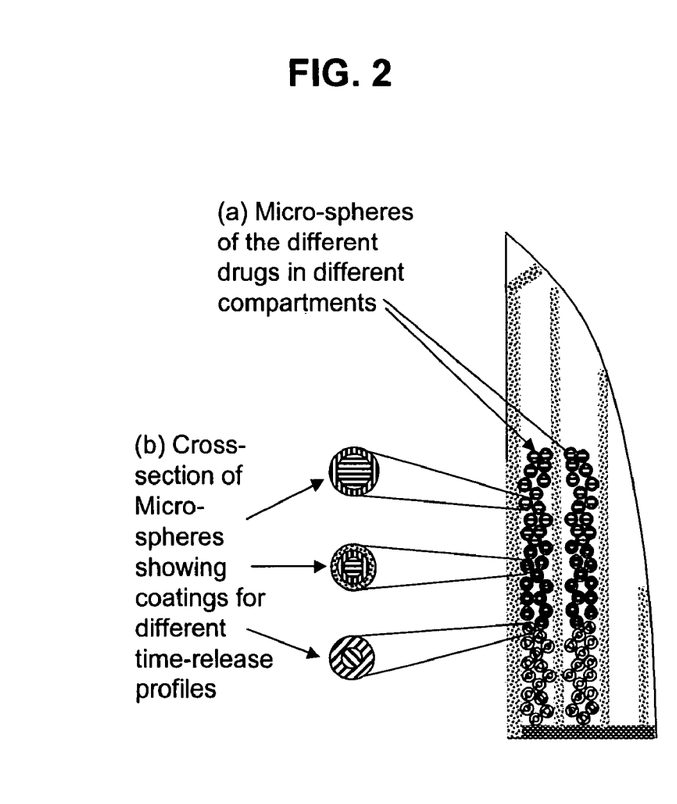
FIG. 2 illustrates two medication compartments of a unified injection package, according to an embodiment of the invention.

FIG. 2 shows a section of the unified ingestion package, specifically two of the medication compartments, each containing micro-spheres (a) of different medications. There may be multiple sets of micro-spheres in a compartment comprising multiple dosages of a medication, each set with a coating designed to provide different time release profiles (b).

Figure 3:
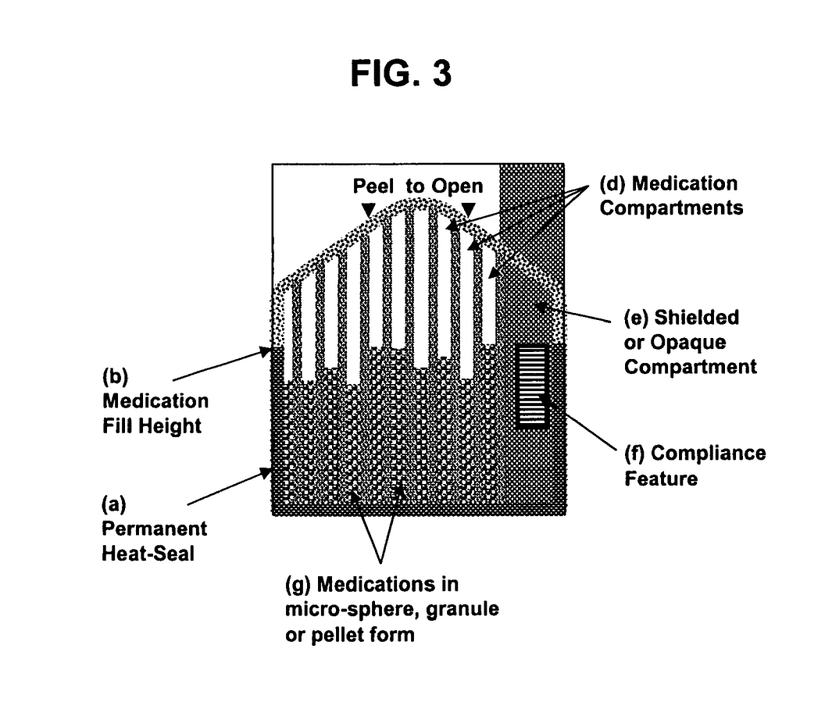
FIG. 3 illustrates a unified injection package that houses multiple sets of coated micro-spheres, according to an embodiment of the invention.

FIG. 3 shows a specific embodiment of the unified ingestion package that houses multiple sets of coated micro-spheres. A permanent heat-seal (a) serves to fasten the two plastic sheets together to form the package and also to provide a maximum fill height (b) for the different medication micro-spheres (g) in the different compartments (d). As in FIG. 1, peel-able heat seal lines (c) form the compartments and seal in the contents, and at least one of the compartments (e) is lined with opaque or shielding material in order to prevent the information embedded in the compliance feature (f) from being perceived without separating the sheets, i.e., opening the package. The compliance feature (e) may be in the form of a card with information printed on it, either as text or barcode that is glued to one of the sheets, or encoded on a magnetic strip or an RFID Tag.

Figure 4:
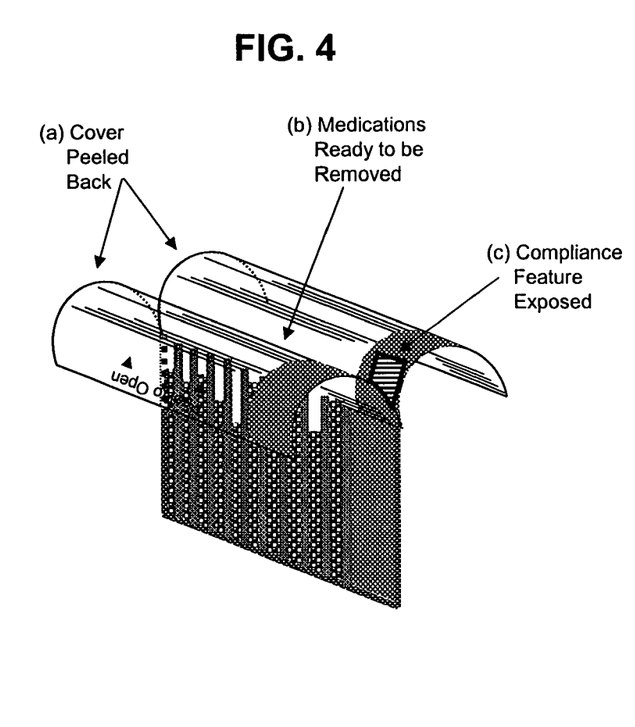
FIG. 4 illustrates steps of a method for using a unified ingestion package, according to an embodiment of the invention.

FIG. 4 shows the method of use of the unified ingestion package. At the appointed unified ingestion time, the patient opens the package by peeling back the two sheets of plastic (a) along the peel-able heat seal lines, up to the point of the permanent heat seal line. At this point, all the medications are ready to be removed (b) by inverting the package into an ingestion medium or vessel. The compliance feature is also exposed (c) at this point, so that it can be perceived by reading the symbols, or using a barcode scanner or a magnetic strip reader, or an RFID reader.

Figure 5A:
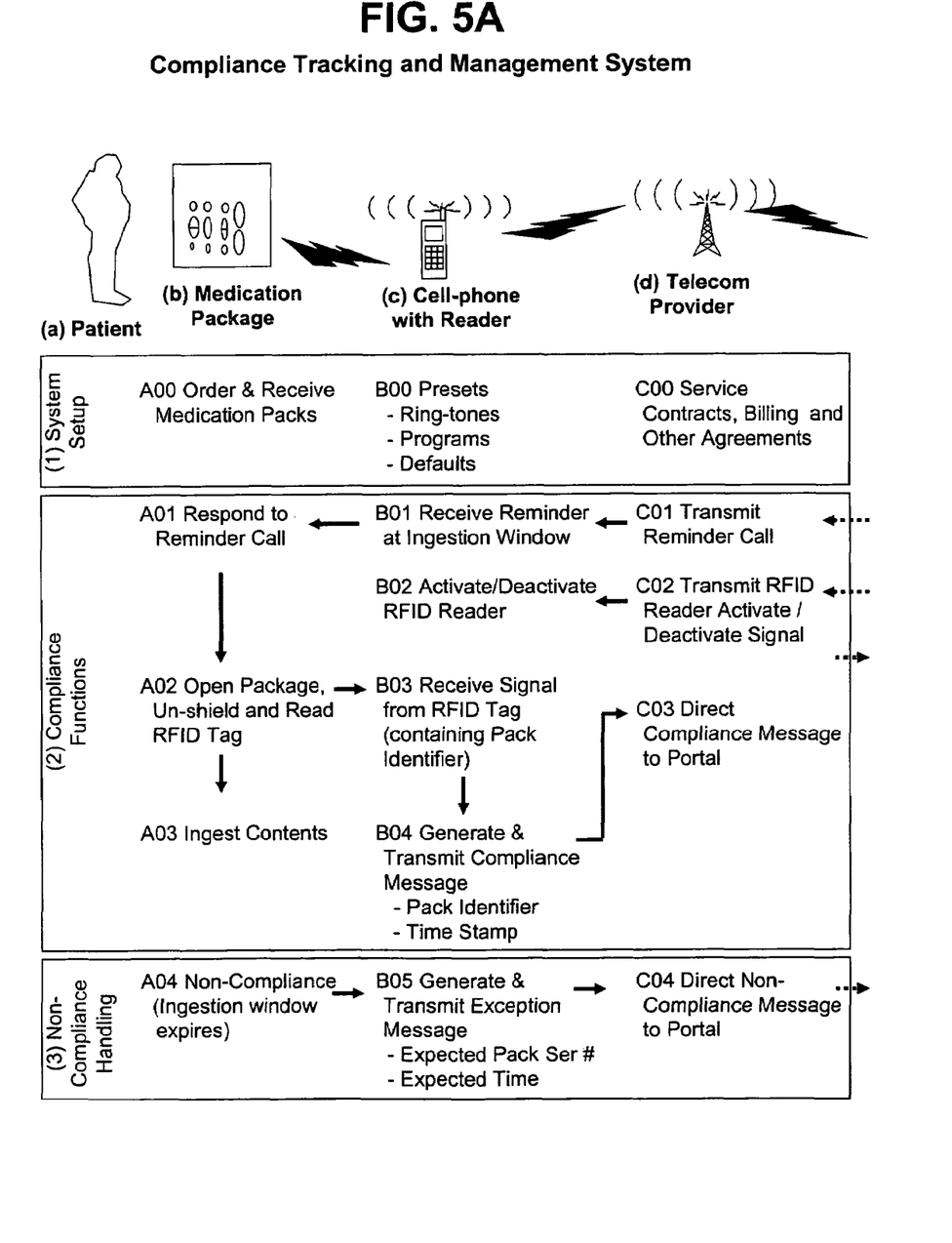
FIG. 5 shows a schematic view of a Compliance Tracking and Management System, according to an embodiment of the invention.
Figure 5B:
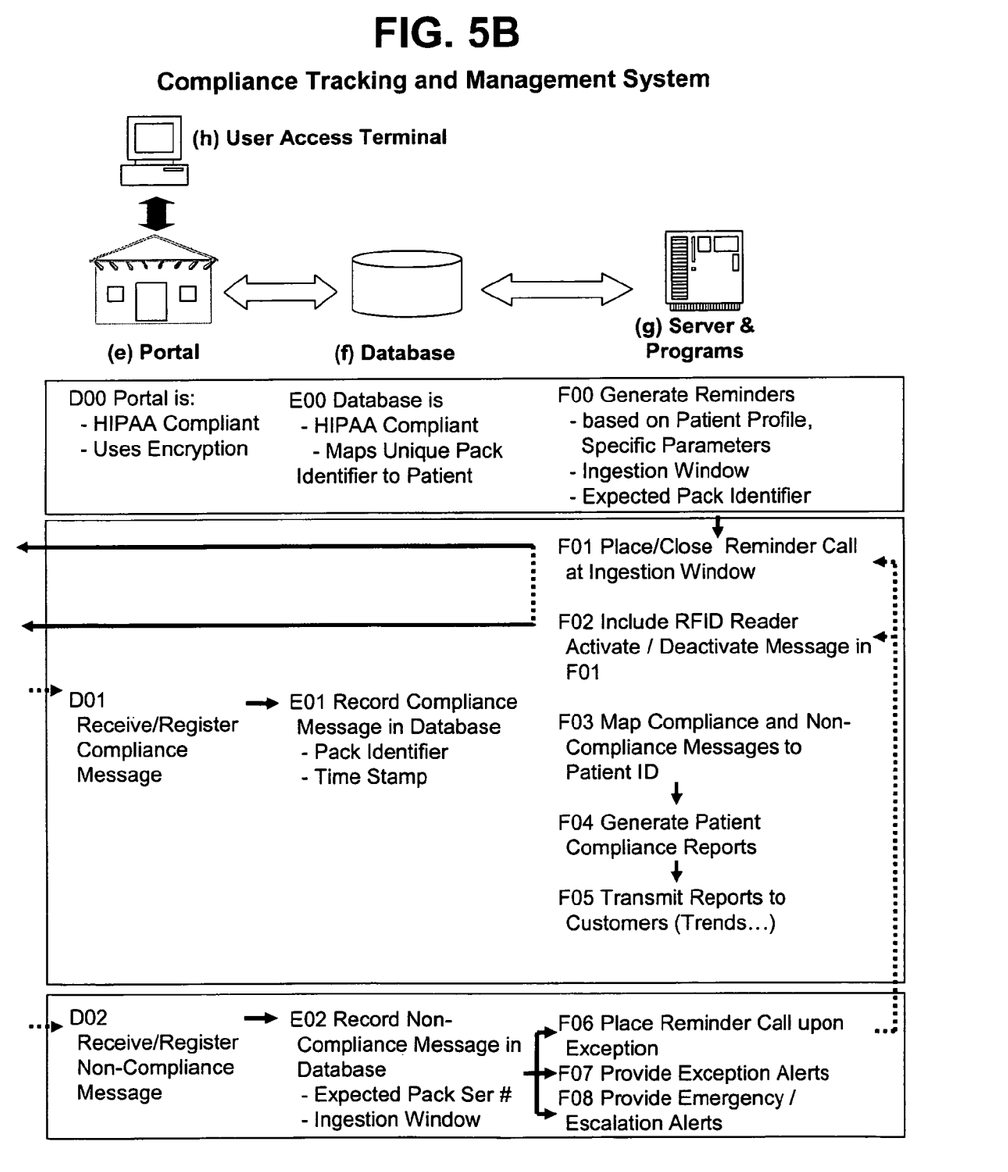

FIG. 5 shows a schematic view of one embodiment of the 'Compliance Tracking and Management System', which uses an RFID Tag as the compliance feature, and which enables the patient (a) to open the medication package (b) as described above, and to use a cell-phone equipped with an RFID reader (c) to record a compliance event. The compliance event information is transmitted via one of several telecom providers (d) to a system portal (e) which communicates to a database (f) and a server with software programs (g). The portal also provides secured access via user access terminals (h). There are system setup elements (1) that represent prerequisites for the proper functioning of the system. The system provides compliance functions (2) and facilities for handling non-compliance (3).

Figure 6:
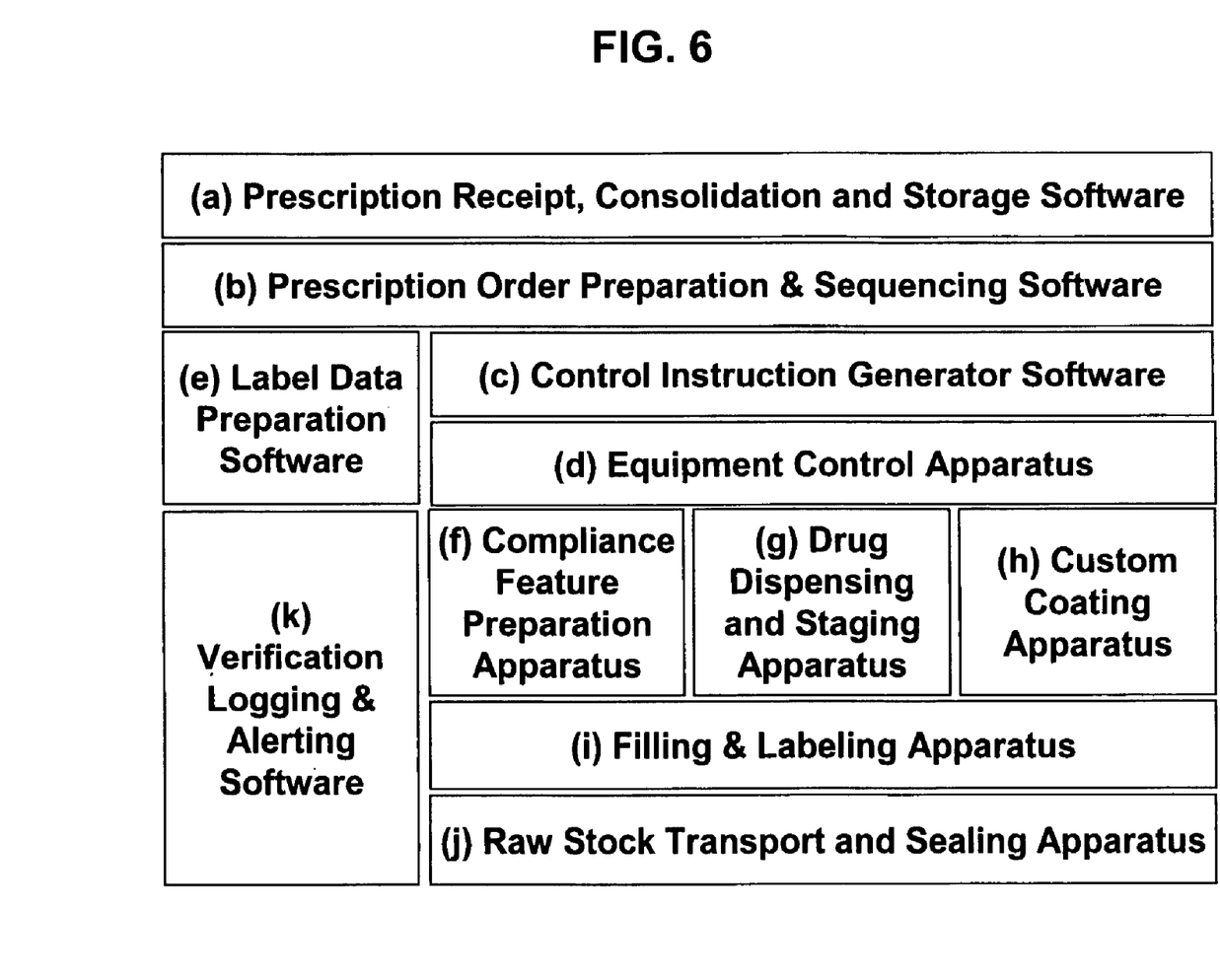
FIG. 6 shows a schematic view of a package production system, according to an embodiment of the invention.

FIG. 6 shows a schematic view of the package production system comprised of: (a) prescription receipt, consolidation and storage software, (b) prescription order preparation and sequencing software, (c) control instruction generator software, (d) label data preparation software, (e) an equipment control apparatus, (f) a compliance feature preparation apparatus, (g) a drug dispensing and staging apparatus, (h) a custom coating apparatus, (i) a filling and labeling apparatus, (j) a raw stock transport and sealing apparatus, and (k) verification logging and alerting software.

Patient-Centric Medication Package

The techniques described herein seek to simplify the taking of medications by combining all the medications that are to be taken by a particular patient, at a particular time of day, into a single "unified ingestion package". The techniques seek to further simplify the taking of medications through a 'one-a-day' unified ingestion package which combines all the medications that are readily available in 'one-a-day' formulations, and needs to be taken only once a day.

Accordingly, a technique and system are provided in which multiple medications are packaged in patient-specific multi-dose packages. For example, assume that a particular patient's prescribed regimen requires three, three and four different medications to be taken in the morning, late afternoon and before bedtime, respectively, on a daily basis. The regimen may be a combination of different medications, or repetitive doses of the same medication, or both, and the regimen may further require some pills to be split or contents of some capsules to be divided. The difficulties in adhering to this type of regimen are obvious. This aspect of the present invention simplifies the taking of these medicines by packaging the three, three and four medications, in the appropriate dose strengths, in three separate multi-dose packs, to be taken in the morning, late afternoon and before bedtime, respectively. Medications that are readily available in 'one-a-day' (extended release or sustained release) formulations may be combined into one of the above multi-dose packs, based on the patient's convenience. As shown in FIG. 1, the package may be constructed in a manner that allows multiple medications to be placed in compartments within the package.

The set of medications that are to be included in the unified ingestion package are referred to herein as the "constituent medications" of the unified ingestion package. If the physical size of the constituent medications is small enough, the unified ingestion package may be a single pill or capsule. Alternatively, the unified ingestion package may be two or more pills or capsules containing the same contents.

A technique and system are provided in which multiple medications are packaged into a multi-dose package in patient-specific, or personalized, time release treatments. According to this embodiment, the unified ingestion package may contain globules or micro-spheres, as shown in FIG. 2, which may be swallowed directly, mixed into an 'ingestion medium' such as a liquid that the patient may then drink, or a semi-solid food such as apple sauce, that the patient may then find easier to swallow. Taste-masking or protective coatings may also be applied to the globules to prevent their dissolution in the ingesting medium.

The coatings enable the medications to be absorbed in the stomach, or to survive the environment in the stomach and then be released in the small intestine, or to further survive the small intestine and later be released in the large intestine. The different time release treatments allow for (1) repeated dosing at regular intervals after ingestion, or (2) dosing at appropriate times of day to improve drug absorption or bio-availability, or (3) introducing appropriate time delays between different interacting medications to minimize the interactions. There may also be requirements to take some of the medications either with or without food. According to one aspect of the invention, a system is provided for treating the medications so that all medications may be taken simultaneously at the same time every day ("unified ingestion time"). With reference to the above example, because each of the ten medications has been treated for time release based on the prescriptions applicable to the specific patient, i.e., the regimen, three of the medications will be released within the patient in the morning, three in the late afternoon and the remaining four at bed-time. Because the patient needs only to remember to take the unified ingestion package at the unified ingestion time every day, the patient is more likely to become habituated and thus adhere to the regimen over an extended period of time.

In another aspect of this invention, if required by a patient's regimen, the contents of the unified ingestion package may include time-release coated globules containing substances that may be considered as 'food', timed to be released at the same time as certain medications that must be taken with food. The food substances may also be timed to be released just before medications that must not be taken on an empty stomach. Alternatively, flavored excipients may be included in the package for taste-masking and improving palatability.

Yet another aspect of this invention serves to more finely titrate the dosages to a specific patient's metabolism and thus personalize the package even further in order to balance the side effects with the therapeutic effects. This is achieved by providing medications in the form of globules that contain a small but standardized amount of the medications, and counting the globules to provide the desired, more precise dosages for a specific patient. Each standardized globule contains the same amount of the medication, within practical limits, which enables the prescribed medication dosages to be metered by counting a specific number of the standardized microscopic globules to add up to the prescribed dosages, or by weighing the standardized globules to provide the requisite dosages. The small standardized amount of medication in each globule permits much finer dosage increments to be prescribed based on titration for specific patients in order to minimize side effects. For example, a patient may require and be able to tolerate somewhere between 50 mg (milligram) and 100 mg of a medication that is currently available only in these increments. The 50 mg dose would be insufficient to address the medical conditions and the 100 mg dose would result in intolerable side effects. However, if the medication were provided so that each globule contained a standardized 1 mg of the medication, then to provide 75 mg (half way between 50 mg and 100 mg) of the medication, we only need to count 75 globules. Alternatively, the requisite 75 mg dosage could be metered by weight of the standardized globules. The dosages can be successively titrated even more finely, say to 65 mg, by monitoring the patient's response and side effects, and adjusting the dosage accordingly.

As shown in FIG. 3, the unified ingestion package may be constructed with multiple compartments, each containing a set of standardized microscopic globules, granules or powder, encapsulated in time-release coatings representing specific medication dosages that are to be released either continuously or in time-spaced intervals. The package may be produced in different shapes and sizes, and may have some or all of the following elements: (1) compartments for medications, food, chemical markers and excipients (2) a specially shielded compartment to house a compliance feature, and (3) other features to help the patient (a) open the package, (b) retrieve the medications and (c) expose the compliance feature. The package is designed to handle different types of medication formulations (pills, capsules, liquids, globules, micro-spheres, etc.) over time, with the same form factor, providing scalability between multiple generations. The package may be produced in a standard ten-compartment version or a version with a customized number of compartments, depending on the need. In the standard version, not all the compartment would necessarily have to be filled; only as many as the number of medications would be, and the rest would be empty.

Individual medications are dispensed in their mass-produced dosage forms such as liquids, pills or capsules into multiple compartments in order to keep interacting medications separated until the package is opened for consumption. For example, capsules may all be placed in a single compartment because the gelatin covering keeps the medications from even touching each other, but pills may be placed in individual compartments to avoid mutual contact, and liquids would be dispensed into individual compartments. Medications for which chemical reactions are not of concern may be placed in the same compartment. Medications in powder, granule or micro-sphere form may also be placed in compartments in a similar manner. In the case where all the medications are coated whether in micro-sphere, granule or powder form, there is little risk of interaction, and all of the medications may be placed in a single compartment, greatly simplifying the design of the package.

The package may be constructed of a water-proof polymer material to keep the medications dry. The material may also have anti-static properties in order to keep drug globules or micro-spheres from sticking to the sides of the package due to electrostatic charge and preventing their complete removal. The material may also have ultraviolet radiation reflecting or absorbing properties to keep the medications from deteriorating. The interiors of the compartments may optionally be coated with gelatin or a similar substance in order to mimic the protective characteristics of a gelatin capsule for drug micro-spheres that are readily available in such capsule form.

The package may be constructed of a heat-sealable polymer in order to provide heat-induced separators between the compartments and to provide tear-off or peel-off heat-seals that allow patients to open the packages. For example, the well-known 'chevron pack' design may be used to facilitate easy opening of the package.

In another embodiment, the package maybe constructed out of gelatin or similar material that dissolves in water, releasing the medication micro-spheres directly into the fluid in the mixing cup. In this case, selected micro-spheres would be coated with a taste-masking material that does not dissolve in water (or the ingestion medium) but dissolves rapidly in the stomach.

The FDA requires that labels clearly indicate several items, such as patient's name, doctor's name, pharmacy's address and phone number, prescription number, and so on. In addition, warning labels and instructions such as 'Do not Take with Alcohol' or 'Take with Food', etc. are also required. In addition, each individual medication name and dosage must be legible on the label. Barcodes of the National Drug Code are also required foe each medication. While much of this information can be printed on the package, the sheer volume of information will require an additional insert or folded label on each package. Alternatively, a label may be attached to the container of the individual packs with all the information and a subset of the information may be printed on each pack. In another embodiment, the entire package may be constructed of gelatin or similar material, and the labeling may be printed using edible inks that are non-toxic and non-allergenic. In this case, the entire package may be dropped into a cup containing an ingestion medium, dissolved in the medium and ingested. The compliance feature may be detached prior to this or retrieved from the ingestion medium. Alternatively, a printed label may be peeled off after ensuring that it is the correct package and before immersing in the ingestion medium. The act of peeling off the label may be used to generate a compliance signal by simultaneously uncovering a compliance feature.

Packages may be color coded to identify when they should be taken. For example a 'white' colored package would identify a morning package, a 'black' colored package would identify a night package and a 'yellow' colored package would identify an afternoon package. Packages may be additionally color-coded or otherwise marked with a clearly visible specific geometric shape specific to an individual patient in a household or facility with multiple patients. Alternatively, the package may have a printed photograph of the patient on the label, subject to applicable regulations. In cases where some medications are optional or have to be taken just before or with meals, supplemental packs may be attached to one of the standard packs.

The unified ingestion time may also be personalized for individual patients based on their preferences and known circadian rhythms. Sometimes medications work better if they are absorbed in the morning versus the evening and vice versa. By providing different time release coatings based on patient convenience or per physician directions, different medications can be timed for release at different times of the day. Excipients, dyes, flavors and additives may also be personalized to patient preferences or to avoid allergic reactions, or additionally, as a way, particularly for pediatric or geriatric patients, to remember which package to take when. For example, strawberry in the morning and chocolate in the evening may serve as an inducement for pediatric patients to take their medicines.

Method of Using the Package

As shown in FIG. 4, a method is provided, through the construction of the package, to: (1) release the medications so they may be removed from their individual compartments and ingested, and (2) expose the compliance feature so a compliance event may be detected or recorded. With reference to the figure, the covers are peeled back to the permanent heat-seal line, at which point, all the peelable heat-seal lines are unsealed up to the level of the permanent heat-seal line. This opens all the compartments. The compliance feature may be read, or removed and activated, and the medications may be removed by emptying the package into a cup for mixing and ingestion.

Compliance Events

Recording patient compliance events—whether patients actually took their medications and at what time of day, is of great interest. Using the compliance event data, physicians would be able to verify that their patients were indeed following their prescriptions properly, insurance companies would be able to verify whether patients were adhering to their regimens and offer incentives to improve adherence (if needed), pharmacies would be able to automatically process and deliver refills based on actual consumption, and so on.

A compliance event can be detected in different stages, namely, (1) opening of the package and emptying of the contents, (2) preparation of the contents before ingestion, for example using a cup to mix the contents with an ingesting medium, and (3) actual ingestion by the patient. The compliance event itself may be captured using manual or automated methods. The package may additionally incorporate features that enable compliance event detection, and methods are also provided to monitor and record compliance events using different types of information such as text, pictures or video.

The compliance number (Unique Package Identifier) would be a sequence of digits with no inherent meaning or association with any patient, and would be transmitted to a patient or caregiver, or incorporated into a compliance feature on a specific package. Prior to transmission or incorporation into a compliance feature, the compliance number would be mapped to a specific package, its intended ingestion time and the respective patient. This association could only be accessed within a secured database. During a compliance event, the compliance number would be received and recorded in a secured database. Subsequently, the compliance number would be mapped back to the respective patient and the intended compliance event, and stored in a secured database. The telephone number from which the compliance number is transmitted, may be used to validate that the package was indeed opened by the intended patient, thus providing a way to immediately detect errors or fraud.

In order to provide incentives for patients to participate, the compliance number may be linked to a rewards system that offers instant prizes, rebates, discount coupons, etc., as well as options for patients to earn compliance points that can be accumulated and redeemed for goods or future medications. The compliance number must be entered within the ingestion window to be eligible for rewards, but may earn points in a six hour window on either side of the ingestion window.

Compliance events are captured in a number of ways: in one embodiment, the 'compliance number' may be transmitted within the cell phone reminder prompt, and the patient prompted to key in the number to confirm compliance. Upon taking the medication, the patient would key in this number either on a website on a cell phone. This would work with conventional medications as well.

In another (visual) method, a camera-phone would be used by the patient to record a still digital picture of the opened package, with the label, including the barcodes, clearly captured so as to indicate without ambiguity, the identity of the opened package, making sure that no false compliance images are sent. The picture would be transmitted to a secured database where the mapping to the patient would occur and the compliance event would be recorded.

Patients may also record images of the prepared contents prior to ingestion, or video clips showing patients in the actual act of ingestion. The images would clearly record the label on the package which would show the patient's name, data and time of ingestion. A time stamp would also be included. These images and data would be encrypted, for privacy reasons and HIPAA compliance, prior to transmission.

In another key aspect of this invention, the unified ingestion package may be constructed to assist in confirming patient compliance to varying degrees of automation. In one embodiment, the package may be constructed to assist in confirming compliance by incorporating a compliance feature that is invisible or hidden in a compartment until it is opened. For example, the compliance number may be printed on the interior surface but shielded from external view by means of an opaque coating or peel-off tab in the compartment. The number would be revealed only after the package has been opened and the contents have been removed in order to read the number or remove the peel-off covering.

The compliance feature may be placed in a compartment with a tear-off covering or a peel-off covering accessible from the interior of the package. For example a barcode may be printed on a small label that is inserted into one of the compartments in a manner that obscures the barcode and prevents it from being scanned until its compartment is uncovered. In another embodiment, a card with a magnetic stripe containing the compliance number would take the place of the printed barcode label. These embodiments make it easier for the patient to enter the compliance number, by merely requiring the patient to scan the barcode or swipe a card with a magnetic stripe instead of manually entering the number.

In yet another embodiment, an RFID tag may be placed in a compartment that is opaque to radio frequencies. Opening the compartment in the package would unshield the tag and allow it to respond to an RFID reader, and this signal would be recorded as a compliance event by a remote compliance monitoring service.

In other embodiments, an RFID sensor, mounted inside a cup would sense changes in resistance when the contents of a package are mixed in the cup with water or other ingestion medium. When interrogated by an RFID reader, the sensor would transmit the changed signal signifying that the contents have been prepared.

In yet another embodiment, a non-toxic marker chemical may be included in the unified ingestion package which would, after ingestion, would produce a color change on the surface of the patient's tongue, or a detectable marker metabolite level in the patient's breath or serum. Changes in tongue color may be recorded and transmitted using a camera-phone or digital camera, along with a time-stamp. Metabolite levels in the breath may be recorded using a breath analyzer enabled cell phone (such as those available from Samsung). Metabolite levels in the serum may be recorded using instruments that may be integrated with a more comprehensive remote patient monitoring system (such as those available from Siemens).

Other package embodiments may include the following:

Titration Packs, Drug or Dose Selector Packs, in which each medication compartment is fitted with a set of breakable internal membranes spaced at set intervals, say at 25 percent increments, along the length of each compartment. Thus these membranes separate the total medication dose into four parts. For example, if the total dose is 100 mg, each increment holds 25 mg. By breaking none, one, two, three or all four membranes, the patient can select a dose of 0, 25, 50, 75 or 100 mg, respectively, of the particular medication. Other compartments may be also fitted in a similar manner, thus providing a way for the patient to select which medication to take and the dosage of each medication individually. Under the guidance of a physician, a patient can thus titrate the dosages of each medication until the proper balance between therapeutic and side effects has been found. Further, the physician can specify a plastic template that can be aligned over the package and pressed to break the appropriate membranes in order to release the desired medications and dosages. The templates may be changed on a daily, weekly or monthly basis by the physician or pharmacist and thus provides a way to change drug regimens even while using the same ingestion package. This pack may also be helpful in cases where the physician wants the patient to skip some medications for a period of time, in which case, the patient would simply not break any of the membranes in the compartments containing the particular medications to be skipped.

Titration for specific patients in order to minimize side effects may be based on techniques such as: (a) Design of Experiments, or (b) Simulated Annealing. The titration method involves: (1) providing the starting dosage strengths of each medication in the form of micro-spheres, (2) monitoring the therapeutic and side effects using a self-referent scale, (3) adjusting the dosages in a predetermined manner and sequence, using micro-spheres, (4) developing a response map for the particular patient, (5) computing the optimum dosages of each medication for the particular patient, and (6) providing the optimum dosages in a package containing the appropriate number or weight of micro-spheres of each medication. Throughout this process, the patient, physician and pharmacist are kept involved, in order to provide clinical oversight.

In clinical trials, study subjects are required to comply with the experimental protocols and take the drugs or placebos as directed. The quality of the trial data is highly dependent on the extent to which the subjects are in compliance with the directions. The system described herein seeks to simplify compliance by providing multiple doses of the medication under study in the form of a unified ingestion package to be taken once a day, at the unified ingestion time. In addition, the exact ingestion time of the package is captured, rather than relying on the reports of the study subjects. The system described herein also enables dose-response studies as well as adaptive trials by providing means to alter the study drug dosage strength or substitution with placebos in an ongoing manner using drug/dose selector packs and templates, or reissuing new trial packs.

Disease-specific Packs (Diabetes pack, Hypertension pack, Cholesterol pack, Polypill pack): in many cases, polypharmacy, or the use of multiple medications, is necessary to bring specific conditions such as serum glucose level or blood pressure under control. As another example, the National Health Service of the UK is considering a 'polypill' that includes of several medications as a prophylactic for people over 55. This invention provides a way to package multiple medications together into disease-specific packs or such 'polypill' packs.

Private Label, Antibiotic Compliance Pack: in this embodiment, the multi-dose packs would contain only the medications manufactured by a specific pharmaceutical manufacturer and its partners, and would carry the manufacturer's label. For example, some antibiotic courses that include one or more medications must be taken for a set period of time in order to prevent the emergence of drug-resistance. Frequently, patients only take partial courses, and discontinue the antibiotics as soon as they start feeling better, resulting in bacteria that develop resistance to the antibiotics. This is a serious concern in the healthcare industry. This system described herein, by providing the entire course in multi-dose packs, by recording compliance events, and by providing reminders, can mitigate this concern.

Travel multi-pack/purse pack: in this embodiment, a number of multi-dose packs would be placed inside a larger pack fitted with an RFID enabled detector that would transmit a signal whenever the pack is opened, thus recording a compliance event. In one embodiment, the individual multi-dose packs would not contain any of the compliance features mentioned above, thus reducing the size of the packs and providing a convenience for travelers, or highly mobile patients. The RFID detector, in this case would be enabled for WiFi transmission.

Alternatively, a cell phone based RFID reader (such as those available from Nokia) would be used to pick up and transmit the compliance events. In a different embodiment, this invention would take the form of a 'Compliance Box' into which conventional medications in bottles would be placed in a box, whose lid would be enabled with a compliance event detection feature similar to the above travel pack.

In yet other embodiments of this invention, the packages may be in different shapes and sizes for different applications. For example, a titration pack may be larger than or of a different shape from a standard pack, not only to house the additional membranes, but also to differentiate it from a regular pack. In further embodiments, the compliance features may be hidden in compartments that can be opened using a tear-off stub rather than having to reach inside the pack to retrieve them. Compliance features may also be hidden in one of the cups in a blister pack.

Reminder System

Reminders improve patient compliance with regimens. Accordingly, techniques are described herein that remind patients automatically to take their medications just before their individual ingestion times on a daily basis. The reminders may be based on voice, text or visual cues and transmitted via telephone, including cell-phone, or the internet. The system may also be customized by the patient to provide different levels of reminding, as some patients may want to be reminded every day, while others may not. The system can also be set to not remind patients when they have been asked to suspend their regular regimen for various reasons such as hospitalization, infection or illness.

The reminder system may use printed material or barcodes or magnetically encoded cards to capture unique compliance events. In one embodiment, the reminder system transmits a 'compliance number' within the reminder message and requires the patient or caregiver to enter the 'compliance number' in the response as a means to confirm that the medications have been taken. This embodiment requires no special packaging and can work with existing medication delivery vehicles such as bottles. In other embodiments, the 'compliance number' is in the form of a unique 'package identifier' that is encoded in other forms such as bar-codes, magnetic strips or RFID Tags, and is captured using the appropriate techniques.

Online "Buddy System"

Without a human touch, reminders tend to become less effective over time. Many patients, especially those who are home-bound, appreciate and respond better when an actual person, particularly a peer, does the reminding. Accordingly, a key aspect of this system provides an automated reminder service that is coupled with an online 'buddy system' for patients to team up and remind each other by phone, with self-selected levels of anonymity, in order to provide a human touch. The levels of anonymity may be adjusted by the patient or buddies at any time. The buddy system could expand to include multiple members who would participate in an online peer group and discuss their experiences. The online peer group would also provide a vehicle to record patient quality-of-life related comments, as well as side-effect information, and the information may be shared with the service, subject to members' permissions.

Compliance Tracking and Management System

As shown in FIG. 5, in one embodiment, the compliance tracking and management system uses RFID Tags, and the different parts of the system perform their respective functions, as described below.

Patient-Related Functions

In order to enable the system to work, there are some prerequisites that must be set up before hand. These include: A00 Order & Receive Medication Packages: (1) get prescription(s) from physician(s), (2) agree to daily ingestion time(s) and/or window(s) as prescribed, (3) register with and order prescribed medications from a certified pharmacy, and (4) receive the medication packages.

Business Rules will be provided as configurable options per the requirements of the service provider, for example: (1) the size of ingestion window may be set at 1 hour or a maximum of 24 hours, as prescribed, and per patient convenience, (2) the start of the ingestion window maybe 5 minutes before the start, (3) the contact attempts at different time intervals and the total number of attempts before escalation, (4) primary, secondary and authorized caregiver telephone numbers, and (5) specific escalation procedures.

Compliance functions are as follows: A01 Respond to Reminder Call: (1) patient receives an automated reminder call before ingestion window, (2) patient answers the call, and (3) patient retrieves the package labeled with the specific ingestion date & time.

A02 Open Package and Un-shield Compliance Feature (RFID Tag): (1) patient opens the pack, which action removes the RFID Tag shielding, and (2) patient uses the RFID reader in the cell phone to read the tag.

A03 Ingest Contents: (1) patient swallows contents of the package along with an appropriate ingestion medium such as water or apple sauce.

Non-Compliance functions are as follows: A04 Non-Compliance Alert: (1) patient ignores reminder call or makes error in taking the reminder call, in which case, the call is repeated, (2) ingestion window expires, in which case, issue a final reminder, renew the window and generate an exception alert, or (3) in case of continued non-compliance even after window has been renewed, generate an escalation alert to inform the predetermined caregiver.

Examples of other exceptions and remedial actions are as follows: (a) patient does not verify correct pack or label is unreadable, in which case, the RFID Tag needs to be re-read, or the patient can enter using the keypad or call the hotline, (b) patient spills contents while opening the package, or misplaces the package, in which case a call to the hotline will reset the next appropriate pack for the present ingestion window, (c) RFID Tag is not read properly, in which case, a voice and/or text message, or a visual, color cue is transmitted to instruct the patient to 'please read tag again'.

Cell Phone Related Functions

In order to enable the system to work, there are some prerequisites that must be set up before hand. These include: B00 Presets—ring-tones, program downloads, and defaults, based on specific patient preferences.

Compliance functions include: B01 Receive Reminder at Ingestion Window: (1) receive call placed by server, based on preset options, such as a special ring-tone for 'it's time to take your medication!' message.

B02 Activate/Deactivate RFID Reader: (1) receive 'activate' signal from server and activate RFID reader, (2) confirm 'active' status to server, (3) receive 'deactivate' signal from server and deactivate RFID reader, and (4) confirm 'inactive' status to server.

B03 Receive Signal from RFID Tag (Unique Package Identifier): (1) read RFID Tag and store in memory, and (2) record date & time of signal storage in memory.

B04 Generate & Transmit Compliance Message comprising: Unique Package Identifier and Time Stamp.

Non-Compliance functions include: B05 Generate & Transmit Exception Message comprising: Unique Package Identifier and Expected Time.

Telecom Service Provider Related Functions

These are part of the providers' standard services: (1) C00 Service Contracts, Billing and Other Agreements, (2) C01 Transmit Reminder Call, (3) C02 Transmit RFID Reader Activate/Deactivate Signal, (4) C03 Direct Compliance Message to System Portal, and (5) C04 Direct Non-Compliance Message to System Portal.

System Portal Functions (1) D01 Receive/Register Compliance Message, (2) D02 Receive/Register Non-Compliance Message. Also, the system portal provides interfaces to user access terminals.

Database Functions

In order to enable the system to work, there are some prerequisites that must be set up before hand. These include: E00 HIPAA compliance, and use of encryption to (1) store patient profiles and (2) map Unique Package Identifier to patient ID, Compliance and Non-compliance functions include: (1) E01 record compliance message in database (Unique Package Identifier, Time Stamp), (2) E02 record non-compliance message in database (Expected Unique Package Identifier, Ingestion Window), Server Functions In order to enable the system to work, there are some prerequisites that must be set up before hand. These include: (1) F00 scan database & generate reminders based on (i) Patient Profile, Patient-Specific Parameters, (ii) Ingestion Window & Expected Unique Package Identifier.

Compliance functions include: (1) F01 place or close reminder call at ingestion window, (2) F02 Include RFID Reader Activate/Deactivate Message in F01, (3) F03 Map Compliance Messages to Patient ID, (4) F04 Generate Patient Compliance Reports, (5) F05 Transmit Reports to Customers, reports such as: (i) Compliance Trends, History, etc., (ii) Actual Drug Consumption & Forecasting, (iii) Automated Reordering information.

Non-compliance functions include: (1) F06 Place Reminder Call upon Exception, (2) F07 Generate Exception Alerts, and (3) F08 Generate Emergency/Escalation Alerts.

Business Rules: HIPAA regulations govern all System functions; all data are secured, access to data is controlled, transmissions do not contain any identifiable data. The compliance database is secured to be compliant with HIPAA regulations. Subject to HIPAA regulations, compliance data that is collected in the database may be provided for examination by authorized parties. Personal or patient data may also be scrubbed from the raw data in order to maintain confidentiality, and then provided for similar examination to yet others.

Decision Support Programs & Analytics

Techniques are also provided to detect whether patients are in compliance on a daily basis. The remote compliance-monitoring service records the date and time of the package-opening signal. If patients have missed taking their medications within a predetermined window after the ingestion time, the system provides a means to automatically record an exception and alerts buddies and designated caregivers so they might take appropriate intervention action.

The system analyzes the database for compliance trends and history for individual patients. Following the applicable regulations, the trends and history may be provided to insurance companies, payers or managed-care organizations. These organizations may further use the information to structure incentives, such as rebates or premium adjustments, to improve the compliance performance of individual patients. Alternatively, the data may be used to more accurately manage risk, as an enabler for consumer-driven healthcare. This data may also be transmitted to providers for use in managing 'Pay-for-Performance' programs.

In another embodiment, the system provides analytics that use patient compliance data as a leading indicator to improve disease management programs. Patient compliance is treated as another vital sign that is captured on a daily basis. When a particular patient stops taking medicines it is only a matter of time before health problems become serious enough to warrant medical attention. Thus compliance data can be useful in identifying which patients are likely to require medical attention if left unattended and disease management programs can proactively stratify risks. Additionally, such patients can be contacted and asked to resume their medications in an attempt to stave of unnecessary medical treatments.

Current supply chain management systems can only track drugs to the pharmacy level. Once the prescriptions are filled and taken from the pharmacy, it is difficult to ensure that the right drugs get to the right patients, outside of a managed facility setting. With the compliance number (keyed-in or uploaded from the compliance feature) provided by the system, and its association with pre-authorized phone numbers, there is a way to quickly detect whether the drugs are being consumed in the intended patient's facility or in a different location, possibly by a different person. Errors and fraud are quickly detected. In further embodiments, a bio-marker such as a fingerprint or iris-scan may be used to authenticate the patient.

The system further reduces non-compliance by tracking the actual consumption of the medications by patients and automatically refilling and delivering them before the patients run out of their medications. Actual consumption data is also fed to pharmaceutical manufacturers, distributors and pharmacies to enable timely and accurate supply replenishment and production forecasting.

In all of the above, as applicable, the patient may be a human or an animal. In the case of animals, the regimen may either be packaged into the food or additionally masked to reduce the olfactory rejection response.

Package Production Equipment

According to another aspect of this invention, a system receives the prescriptions and rules for any number of patients and accordingly dispenses the appropriate medications into patient-specific, labeled unified ingestion packages. In another embodiment, the system receives a specific patient's prescriptions and rules, and accordingly dispenses the appropriate medications into the patient-specific, labeled unified ingestion packages.

As shown in FIG. 6, one embodiment of the system includes: (a) prescription receipt, consolidation and storage software, (b) prescription order preparation and sequencing software, (c) control instruction generator software, (d) label data preparation software, (e) an equipment control apparatus, (f) a compliance feature preparation apparatus, (g) a drug dispensing and staging apparatus, (h) a custom coating apparatus, (i) a filling and labeling apparatus, (j) a raw stock transport and sealing apparatus, and (k) verification logging and alerting software.

The Prescription Receipt, Consolidation And Storage Software electronically receives and stores prescriptions for any number of patients, from any number of physicians or other authorized prescribers, on a hard drive that is secured from access by unauthorized parties. For individual patients, the software then consolidates the prescriptions that are relevant to their respective upcoming regimen periods (30, 60 or 90 days).

Next, the Prescription Order Preparation And Sequencing Software prepares consolidated prescription orders, or 'regimens' for each patient specifying: (1) labeling elements such as (a) patient name, (b) physicians' names and DEA numbers, and (c) other legally required elements, (2) prescription identifiers such as (a) drug names and respective dosages, (b) respective time release delays after ingestion, (c) number of packages, (d) regimen start and end dates and times, (e) other required elements such as drug information sheets, (f) claims information for payers, and (g) invoices. It then sequences individual patients' regimens (based on delivery dates) and transmits individual patient regimens to the control instruction generator software.

The Control Instruction Generator Software generates specific instructions, per the consolidated prescription for a particular patient, for: (1) label data preparation, (2) compliance feature preparation, (3) drug dispensing and staging, (4) custom coating, (5) filling and labeling and (6) raw stock transport and sealing. The control instructions and transmitted to the 'Equipment Control Apparatus'.

The Custom Coating Apparatus provides a means for applying time-release coatings on selected sets of micro-spheres, based on specific instructions from the Control Instruction Generator Software. The software may also check regimens for drug interactions and generate instructions to treat selected micro-spheres with time-delay coatings.

The Label Data Preparation Software receives labeling information, including all the labeling elements described earlier, for a particular patient, from the 'equipment control unit' and generates instructions for the labeling device that is part of the 'filling and labeling unit'.

The Compliance Feature Preparation Apparatus receives a set of 'compliance numbers', for a particular patient, for a sequence of planned compliance event (ingestion date and time). Each compliance number is incorporated into a compliance feature that is to be placed into the shielded compartment of a particular package. This may be accomplished in multiple ways, as described above, including: (1) printing the number on a card or label, (2) printing a bar code on a card or label, (3) programming the number into a magnetic strip on a card, or (4) programming the number into an RFID tag. Depending on the method used, a corresponding device will be incorporated into the system. This task is performed in synchronization with the package label data preparation.

The Drug Dispensing and Staging Apparatus: based on a particular patient's medications and dosages, this unit first verifies that the correct medications and dosages are being provided (by scanning the bar codes on the bulk drug containers), then removes the appropriate tablets or capsules from the bulk containers. This unit then dispenses and assembles all the tablets and capsules that are to be placed in a particular package, in synchronization with the label data preparation and compliance feature preparation operations for the same package.

The Filling and Labeling Apparatus receives the labeling information for a specific package and prints the information on predetermined places on the package. It then receives the pre-sorted tablets, capsules, or micro-spheres, for a particular package, as well as the prepared compliance feature, and places them in appropriate compartments in the empty package stock.

Equipment are available to dispense multiple medications in standard tablet or capsule form into multi-dose packages and labels the packages for specific patients and ingestion times. The system described herein will augment the above available equipment with a distinct dispensing unit that pre-assembles the different oral medications, based on a specific patient's regimen, that are to be placed in each multi-dose package. During preassembly, medications that can be placed in the same compartment are sorted and placed in separate funnels, one for each compartment in the package. In addition, the system will modify the available equipment to prepare and place the compliance feature in a shielded compartment of the package.

Further, the modified equipment may be coupled with other available robots that automatically fetch the appropriate medications for a patient from an array of standard medications.

Based on the particular regimen being prepared, the relevant medications, in bulk form, are retrieved and staged (manually or using a robot). The barcode on each bulk medication container is scanned to verify that it is the right medication for the given regimen, and the verification event is logged. If errors are found, alerts are issued immediately which must be rectified before the dispensing can proceed.

Drugs in micro-sphere form: in a different embodiment, the medications may be provided in micro-sphere form (or coated globules or powder form). The micro-spheres would be specified to provide: (1) identical amounts of medication within a certain tolerance, (2) coatings to release the medication in specified times after ingestion, (3) coatings to prevent dissolution in ingestion media, etc. Micro-spheres would be tested and certified before acceptance for dispensing.

The system described herein provides a distinct dispensing unit that meters appropriate medications, based on a patient's prescriptions, by counting or weighing the micro-spheres, granules or powders, and places each medication in a separate funnel, one for each compartment in the package. By inserting each funnel into a different compartment in the raw package and vibrating the funnels, each medication is placed in the respective compartment. The system then verifies and records that the drugs have been dispensed as prescribed and the dispensing unit is clean, as follows. When the medications have been placed in their respective compartments, each funnel is weighed to make sure that there is no residual medication in the funnel. The vibration is then continued for a predetermined period in an attempt to dislodge any residual medication.

The Raw Stock Transport And Spooling Apparatus: this is usually part of available packaging equipment and serves to feed the raw (empty) package stock to the filling Verification Log and Alerting Software: records and maintains the prescription and verification records for (1) dispensing, (2) compliance feature preparation, (3) labeling, (4) package filling, and (5) equipment clean-up and reset for the next prescription. The unit also alerts the operator in case of error, and provides options for error recovery, such as when the weight of a dispensing funnel indicates residual medication even after vibration during filling.

According to another aspect of the invention, a system receives prescription rules for any number of patients and applies different time release treatments to the same base medications in order to generate patient-specific, properly labeled unified ingestion packages for each patient based on the prescription rules (regimen) for the patient.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A method for reducing non-compliance of medication use, the method comprising:
    generating and storing an identifier for each dosage instance of a plurality of dosage instances that are associated with a specific patient;
    wherein the step of generating an identifier for each dosage instance includes generating a first identifier for a first dosage instance;
    wherein the identifier generated for each dosage instance of the plurality of dosage instances is unique relative to identifiers provided to the specific patient for any other dosage instance of the plurality of dosage instances; and
    wherein each dosage instance, of the plurality of dosage instances, corresponds to a specific period of time at which the specific patient is prescribed to take medications;
    wherein the specific patient is prescribed to take a plurality of medications at the first dosage instance of the plurality of dosage instances;
    wherein the medications for each dosage instance are contained in microspheres, granules, or pellets;
    wherein the microspheres, granules or pellets that contain the medications for each dosage instance include multiple subsets of microspheres, granules or pellets;
    wherein each subset is customized to contain a specific dosage of a specific medication for the specific patient;
    wherein all subsets for each dosage instance are for consumption during the specific period of time that corresponds to the dosage instance;
    creating a package that includes a mechanism for conveying the first identifier for the first dosage instance;
    placing in the package the microspheres, granules or pellets that contain the medications for the first dosage instance for the specific patient;
    wherein at least one of the subsets for said first dosage instance is designed for time release; and
    sealing the microspheres, granules or pellets that contain the medications for the first dosage instance for the specific patient within the package in a manner that prevents the first identifier from being perceived from the mechanism until the package is opened.

2. The method of claim 1 further comprising:
    capturing identifiers associated with each of one or more dosage instances of the specific patient, and
    analyzing a set of captured identifiers to characterize a specific patient's compliance behavior.

3. The method of claim 2 further comprising predicting probable medical outcomes based on characterization of the specific patient's compliance behavior.

4. The method of claim 1 wherein:
    the steps of generating, creating, placing and sealing are performed for each patient of a plurality of patients; and
    the identifier generated for each specific dosage instance for each specific patient is unique relative to all other identifiers generated for other patients.

5. The method of claim 1 wherein:
    the steps of generating, creating, placing and sealing are performed for each patient of a plurality of patients;
    the identifier generated for each specific dosage instance for each specific patient is not unique relative to all other identifiers generated for other patients; and
    the identifier generated for each specific dosage instance for each specific patient is combined with another number associated with the specific patient to create a composite identifier that is unique relative to all other identifiers generated for other patients.

6. The method of claim 5 further comprising:
    receiving an indication of the identifier through a communication; and
    capturing the number associated with the specific patient from the communication.

7. The method of claim 6 wherein:
    the step of receiving an indication of the identifier through a communication includes receiving an indication of the identifier by a telephone communication; and the step of capturing the number associated with the specific patient from the communication includes capturing caller identifier information associated with the telephone communication.

8. The method of claim 1 further comprising:

communicating a reminder to the specific patient, wherein the reminder is associated with the first dosage instance; and determining whether the specific patient has complied with taking the set of medications at the first dosage instance based on whether the identifier is received in response to the reminder.

9. The method of claim 8 wherein:

the step of communicating a reminder includes using an automated compliance system to send a text message to a cell phone of the specific patient; and the step of determining whether the specific patient has complied with taking the medications at the first dosage instance is based on whether the automated compliance system receives a response, to the text message, that includes the identifier.

10. The method of claim 1 further comprising an automated compliance system determining whether the specific patient has complied with taking the medications at the specific dosage instance based on whether the automated compliance system receives a communication that includes the identifier prior to a predetermined deadline.

11. The method of claim 1 further comprising an automated compliance system determining whether the specific patient has complied with taking the medications at the specific dosage instance based on whether the automated compliance system receives a communication that includes the identifier within a predetermined window of time before and after the prescribed time of the specific dosage instance.

12. The method of claim 1 wherein:

the mechanism is an RFID Tag, and the step of sealing the medications within the package in a manner that prevents the identifier from being perceived from the mechanism until the package is opened includes sealing the package in a manner that shields the RFID Tag.

13. The method of claim 12 wherein the step of sealing the package in a manner that shields the RFID Tag includes covering the RFID Tag with a material that shields the RFID Tag.

14. The method of claim 1 wherein:

the mechanism is printed material from which the identifier may be visually perceived, and the step of sealing the set of medications within the package in a manner that prevents the identifier from being perceived from the mechanism until the package is opened includes sealing the package in a manner that prevents the printed material from being visually perceived.

15. The method of claim 14 wherein the identifier is printed on the printed material using human-readable symbols.

16. The method of claim 14 wherein the identifier is printed on the printed material using a bar code.

17. The method of claim 1 wherein:

the mechanism is a magnetic strip on a card material, and the step of sealing the set of medications within the package in a manner that prevents the identifier from being perceived from the mechanism until the package is opened includes sealing the package in a manner using a material that shields the magnetic strip.

18. The method of claim 1 wherein:

each subset of micro-spheres, granules or pellets comprising a specific dosage of a specific medication, is treated with a time-release coating that delays the release, in the patient's body, of the specific medication for a specific time after ingestion.

19. The method of claim 18 wherein:

a first subset of micro-spheres, granules or pellets is treated with the time-release coating that delays the release until a first time;

a second subset of micro-spheres, granules or pellets is treated with the time-release coating that delays the release until a second time that is different than the first time; and the first subset and the second subset are prescribed to be taken by the specific patient at said specific dosage instance.

20. The method of claim 1 wherein the specific period of time corresponds to a specific date and a specific time.

* * * * *